United States Patent [19]

Szmuszkovicz

[11] 4,217,362
[45] Aug. 12, 1980

[54] ANILIDE DERIVATIVES AS ANTIDEPRESSANTS

[75] Inventor: Jacob Szmuszkovicz, Kalamazoo, Mich.

[73] Assignee: The Upjohn Company, Kalamazoo, Mich.

[21] Appl. No.: 930,690

[22] Filed: Aug. 3, 1978

Related U.S. Application Data

[60] Division of Ser. No. 796,989, May 16, 1977, Pat. No. 4,128,663, which is a continuation-in-part of Ser. No. 777,599, Mar. 15, 1977, abandoned, which is a continuation-in-part of Ser. No. 746,191, Nov. 30, 1976, abandoned.

[51] Int. Cl.$^2$ .................... A61K 31/24; C07C 103/38
[52] U.S. Cl. ............................. 424/309; 260/561 B; 260/562 A; 424/308; 424/311; 424/314; 424/324; 260/107
[58] Field of Search ............................. 560/107, 250; 260/561 B, 562 A; 424/308, 309, 311, 314, 324

[56]  References Cited

U.S. PATENT DOCUMENTS

| | | | |
|---|---|---|---|
| 3,510,492 | 5/1970 | Szmuszkovicz | 260/293 |
| 3,852,058 | 12/1974 | Huffman | 260/562 R |
| 4,098,904 | 7/1978 | Szmuszkovicz | 260/465 D |

OTHER PUBLICATIONS

Gordon et al., The Chemists Companion, J. Wiley & Sons, N.Y., N.Y., 1972, pp. 144–155.

Primary Examiner—Arthur P. Demers
Attorney, Agent, or Firm—John T. Reynolds

[57]  ABSTRACT

Anilide derivative compounds of the formula

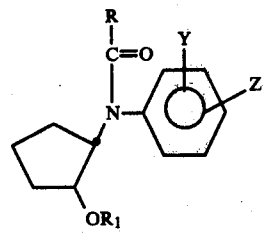

e.g., trans-N-(2-hydroxycyclopentyl)-3',4'-dichloropropionanilide, have been found to possess potent Central Nervous System (CNS) antidepressant properties.

These compounds are promising antidepressant drugs which are characterized by less toxicity than imipramine, and long-acting activity which may allow longer durations between administrations, e.g., once a day. Pharmaceutical compositions containing these compounds and a process for treating conditions of depression with these compositions are also disclosed.

4 Claims, No Drawings

ANILIDE DERIVATIVES AS ANTIDEPRESSANTS

CROSS REFERENCES TO OTHER APPLICATIONS

This is a division of application Ser. No. 796,989, filed May 16, 1977, now U.S. Pat. No. 4,128,663, which was a continuation-in-part of application Ser. No. 777,599, filed Mar. 15, 1977, now abandoned, which was a continuation-in-part of Ser. No. 746,191, filed Nov. 30, 1976, now abandoned.

INTRODUCTION

This invention relates to some cycloaliphatic amides which have central nervous system pharmaceutical utility. More particularly, this invention provides some new N-(2-hydroxy, 2-alkyloxy-, 2-aralkyloxy-, or 2-acyloxy cyclopentyl)-N-alkanoylanilide derivative compounds, which have been found to have potent CNS antidepressant properties, which make them useful as antidepressant drugs when formulated into useful pharmaceutically usable composition forms and administered in appropriate dosages.

BACKGROUND OF THE INVENTION

W. G. Stoil et al., in *Helvetica Chemica Acta*, Vol. 34 (1951), pp. 1937 to 1943, disclose N-[2-(dimethylamino)-cyclohexyl]aniline and procedures for making it from N-(2-hydroxycyclohexyl)aniline and suggest that the compounds therein have antihistamine pharmacological properties, but nothing is said about the compounds of this invention or their use as antidepressant drugs.

J. W. Lewis et al., in an article entitled "The Reactions of Aromatic Nitroso-compounds with Enamines. Part I. The Reaction of Nitrosobenzene With 1-Morpholin-1-cyclohexene" in *J. Chem. Soc.* (London) (1972), Perkins Transactions I, Part III, pp. 2521–2524, discloses inter alia N-(2-morpholin-1-yl-cyclohexyl)-phenylhydroxylamine and its hydrochloride salt, but it does not disclose or suggest the alkanoyl-anilide derivatives of this invention or their antidepressant properties.

J. W. Lewis et al., in an article entitled "Chemistry and Biological Activity of N-Substituted Hydroxylamines" in *J. Pharmaceutical Sciences*, December, 1974, Vol. 63, No. 12, pp. 1951–1953, discloses some N-Arylhydroxylamines such as N-[2-(N-pyrrolidinyl)cyclohexyl]-N-phenylhydroxylamine but these do not have useful CNS properties. Diuretic activity is alleged therein for the alcohols such as [2-(N-piperidinylcyclohexyl)(4-methoxyphenyl)methanol] and when the alcohol is acetylated, CNS depressant activity is said to appear. It also discloses the reaction of propionyl chloride with N-[2-(N-piperidinyl)-1,1-dimethylethyl]-N-phenylhydroxylamine to form the N-chloro compound which is then converted to a mixture of chlorinated aniline derivatives. That publication does not teach the compounds disclosed herein, how to make them, nor does it suggest the antidepressant properties which have been found for the compounds disclosed and claimed herein.

Szmuszkovicz U.S. Pat. No. 3,510,492 discloses and claims some 2-anilino- and 2-anilinomethylcycloalkylamines which are useful as antidiabetic drugs in that they can be administered in low dosages to reduce blood sugar. In column 3 this Szmuszkovicz patent discloses a Method B for preparing the N-(2-aminocycloalkyl)anilines of that invention and discloses the making and use of some N-(2-oxocycloalkyl)anilines (structure VI) compounds as chemical intermediates therein. Further, in column 3 thereof, that Szmuszkovicz patent discloses some N-(2-carboxycycloalkyl)anilines (structure XI) as chemical intermediates in the process for preparing Szmuszkovicz's cis-N-(2-aminocycloalkyl)anilines of that patent. In column 10 thereof, Szmuszkovicz discloses some 2-hydroxycycloalkylamines as chemical intermediates in disclosing how to prepare the starting materials for the compounds claimed therein. However, that patent does not disclose or suggest the compounds of this invention, how to prepare them or what pharmaceutical utilities they might have.

In my patent applications Ser. Nos. 746,191, filed Nov. 30, 1976, now abandoned and 777,759, filed Mar. 15, 1977, now abandoned I have disclosed and claimed the use of some N-(2-aminocyclopentyl)-N-alkanoxylanilides and their 2-N-oxides as antidepressant drugs. Those compounds are characterized by a cyclopentane-1,2-di-nitrogen structure, whereas the compounds of this invention are characterized by having an oxygen bonded to the cyclopentane ring carbon atom in the 2-position thereof.

Those in the pharmaceutical, chemical and pharmacological arts continue to need and look for active and more economical drugs which will have useful Central Nervous System (CNS) drug properties.

OBJECTS OF THE INVENTION

It is an object of this invention to provide some new N-(2-hydroxycyclopentyl)anilide compounds and ether and ester derivatives thereof which have promising CNS antidepressant drug properties and uses as chemical intermediates to prepare N-(2-aminocyclopentyl)anilide antidepressant drug compounds.

It is a more specific object of this invention to provide some new N-(2-hydroxycyclopentyl)-N-alkanoylanilides which are useful as antidepressant drugs, the preferred compounds having less toxicity than imipramine and long activity which allows longer durations between administrations.

It is another object of this invention to provide compositions, useful in pharmaceutical dosage unit form, for treating conditions of depression in mammals including humans comprising an N-(2-hydroxycyclopentyl)-N-alkanoylanilide, or an ether or ester thereof, as described herein, in a pharmaceutical carrier.

It is another object of this invention to provide a process or method for treating conditions of depression in mammals including humans with an effective, non-toxic amount of these compositions containing an N-(2-hydroxycyclopentyl)-N-alkanoylanilide, or an ether or ester thereof.

Other objects, aspects and advantages of this invention will become apparent from reading the remaining specification and claims which follow.

SUMMARY OF THE INVENTION

This invention provides some N-(2-hydroxycyclopentyl)-N-alkanoylanilides and ether and ester compounds, as described more fully below, as new compounds. These compounds have been found to be useful as CNS antidepressant drugs, in standard laboratory animals to measure those properties. These new compounds are also chemical intermediates for the preparation of N-(2-aminocyclopentyl)-N-alkanoylanilide antidepressant drug compounds referred to in my above-identified patent applications. All of these compounds are characterized by lower toxicity than imipramine and have long acting activity which permits longer duration between administrations than other known anti-depressant drugs.

This invention also includes pharmaceutical compositions containing an N-(2-hydroxycyclopentyl)-N-alkanoylanilide, or an ether or an ester thereof, in a pharmaceutical carrier, which compositions are useful in pharmaceutical dosage unit form for treating conditions of depression in mammals including humans. This invention also includes a method of using these compositions to treat conditions of depression in mammals including humans by administering to such a patient suffering conditions of depression an effective, nontoxic amount of an N-(2-hydroxycyclopentyl)-N-alkanoylanilide or an ether or ester thereof, as described herein, or a pharmaceutical carrier.

DETAILED DESCRIPTION OF THE INVENTION

More specifically, this invention provides compounds of the formula

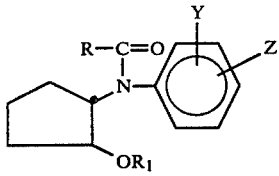

I wherein the heavy dot • at the 1-position carbon atom of the cyclopentyl ring denotes trans-configuration relative to the oxygen group (—OR$_1$) in the 2-position of the cyclopentyl ring:

R is hydrogen,
  C$_1$ to C$_3$-alkyl, C$_3$ to C$_6$-cycloalkyl, C$_1$-C$_3$ alkyloxy, C$_2$ to C$_4$-alkenyl, or C$_1$ to C$_3$-alkyloxymethyl;

R$_1$ is hydrogen, C$_1$ to C$_3$-alkyl, C$_3$ to C$_5$-(allylic)alkenyl, the benzyl group

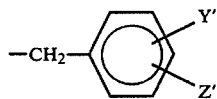

where Y' and Z' are as defined below, or the group

wherein R$_2$ is hydrogen,
  C$_1$ to C$_3$-alkyl, benzyl, as indicated above, or a phenyl group

wherein Y' and Z' are as defined below; and each of Y, Z, Y' and Z' is a substituent, preferably at least one of which is in the 3- or 4-position, having a Hammett substituent constant, sigma meta ($\sigma_m$), in the range of from about −0.1 to +0.6 or a Hammett substituent constant sigma para ($\sigma_p$) in the range of from about −0.3 to about +0.8 as compiled by A. G. Gordon and R. A. Ford in *The Chemist's Companion: A Handbook of Practical Data, Techniques and References*, J. Wiley & Sons, N. Y. (1972) pp. 144 to 155, for example, hydrogen, a halogen having an atomic number of from 9 to 35, trifluoromethyl, C$_1$ to C$_3$-alkyl, and C$_1$ to C$_3$-alkyloxy, azido, or some equivalent group, and the Y, Z or Y' and Z' can be the same or different, and Y, Z or Y' and Z' are not necessarily the same at the same time.

The compounds in their crystalline state can be isolated from reaction mixtures as solvates, i.e., with a discrete quantity of solvent, e.g., water, ethanol, and the like, associated physically, and thus the solvent is removable without effective alteration of the chemical entity per se, and are included with the compounds per se herein.

In the above formula I compounds the term "C$_1$ to C$_3$-alkyl" means methyl, ethyl, n-propyl and isopropyl; the term "C$_3$ to C$_6$-cycloalkyl" means cyclopropyl, cyclobutyl, cyclopentyl and cyclohexyl groups; the term "C$_2$ to C$_4$-alkenyl" includes, for example, vinyl, allyl, 2-butenyl, 1-propenyl, and the like. The halogens having atomic numbers of from 9 to 35 are fluorine, chlorine and bromine. The term "C$_3$ to C$_5$-(allylic)alkenyl" includes the non-adjacent double bond groups, e.g., allyl, 2-propenyl, 2-methyl-2-butenyl, 2-pentenyl, and the like; the term "C$_1$-C$_3$ alkyloxy" includes, e.g., methoxy, ethoxy, propoxy; the term "C$_1$-C$_3$ alkyloxymethyl" includes, e.g., methoxymethyl, ethoxymethyl, n-propyloxymethyl, and the like.

A preferred group of compounds of formula I are those wherein R is C$_1$ to C$_3$-alkyl, R$_1$ is hydrogen and at least one of Y and Z is a halogen having an atomic number of from 9 to 35, preferably in the 3- or 4-positions, trifluoromethyl, or a C$_1$-C$_3$-alkyl. Examples of such compounds include the trans isomers of:

3,4-Dichloro-N-(2-hydroxycyclopentyl)propionanilide,
4-Bromo-N-(2-hydroxycyclopentyl)propionanilide,
3,4-Difluoro-N-(2-hydroxycyclopentyl)butyranilide,
3-Trifluoromethyl-N-(2-hydroxycyclopentyl)propionanilide,
3-Bromo-4-ethyl-N-(2-hydroxycyclopenty)acetanilide,
4-Chloro-3-methyl-N-(2-hydroxycyclopentyl)propionanilide,
and the like.

Another preferred group of such formula I compounds are those wherein R is C$_1$ to C$_3$-alkyl, R$_1$ is C$_1$ to C$_3$-alkyl and at least one of Y and Z is a halogen having an atomic number of from 9 to 35, preferably in the 3- or 4-position, trifluoromethyl, or a C$_1$-C$_3$ alkyl. Examples of such compounds, include the trans isomers of:

3,4-Dichloro-N-(2-methoxycyclopentyl)propionanilide,
4-Bromo-N-(2-ethoxycyclopentyl)propionanilide,
3-Trifluoromethyl-N-(2-propoxycyclopentyl)butyranilide, and
3-Chloro-4-methyl-N-(2-methoxycyclopentyl)propionanilide, and the like.

Another preferred group of the formula I compounds are those wherein R is C$_3$ to C$_6$-cycloalkyl, R$_1$ is C$_1$ to C$_3$-alkyl and at least one of Y and Z is a halogen having an atomic number of from 9 to 35, preferably in the 3- or 4-position, trifluoromethyl, or C$_1$-C$_3$ alkyl. Examples of such compounds include:

3,4-Dichloro-N-(2-methoxycyclopentyl)cyclopropanecarboxanilide,
4-Bromo-N-(2-ethoxycyclopentyl)cyclobutanecarboxanilide, 3-Trifluoromethyl-N-(2-propoxycyclopentyl)cyclopentanecarboxanilide,
3-Chloro-4-methyl-N-(2-methoxycyclopentyl)cyclohexanecarboxanilide, and the like.

Another preferred group of formula I compounds of this invention are those wherein R is $C_1$ to $C_3$-alkyl, $R_1$ is $C_1$ to $C_3$-alkanoyl and at least one of Y and Z is a halogen having an atomic number of from 9 to 35, preferably in the 3- or 4-position, trifluoromethyl, or $C_1$-$C_3$ alkyl. Examples of such compounds include the trans isomers of:

3,4-Dichloro-N-(2-acetoxycyclopentyl)-N-acetanilide,
3,4-Dichloro-N-(2-acetoxycyclopentyl)-N-propionanilide,
4-Bromo-N-(2-propionoxycyclopentyl)-N-propionanilide,
3-Trifluoromethyl-N-(2-formyloxycyclopentyl)-N-propionanilide, and
3-Chloro-4-methyl-N-(2-acetoxycyclopentyl)-N-propionanilide.

The various compounds of formula I above can be prepared by a series of process steps starting from 1,2-cyclopentene oxide and the desired aniline or substituted aniline to form the trans 1-anilino-2-hydroxycyclopentanes of the formula

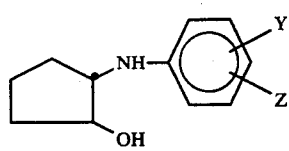

These trans 1-anilino-2-hydroxycyclopentanes are then reacted with an R—C(O)X acyl halide or R—C(O)—O—C(O)—R acid anhydride to form the N-acylamides of the formula

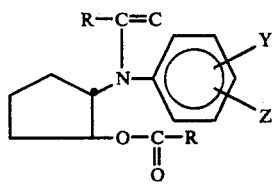

wherein R, Y and Z are as defined above, and may or may not be the same as $R_2$, depending upon the ester-amide product desired. If it is desired to proceed further to prepare the alcohol-amide products, the above ester amides are subjected to basic hydrolysis to form the new compounds of the formula

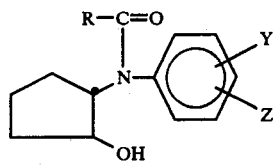

wherein R, Y and Z are as defined above. These alcoholamide products may be used as the products of this invention or they can be used as chemical intermediates by reaction thereof with an $R_1X$ halide wherein $R_1$ is as defined above and X is chlorine or bromine to form the ether-amide compounds of the formula

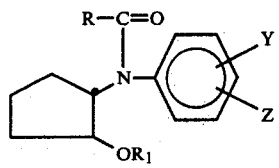

wherein $R_1$ denotes the residue of the ether groups defined above, and R, Y and Z are as defined above, or the alcohol-amide compounds can be reacted with an $R_2$—C(O)X acyl halide to form new ester-amides of the formula

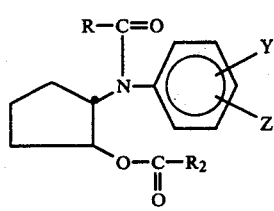

where $R_2$ denotes the residue of the N-acyl groups defined above, and R, Y and Z are as defined above. This latter esterification step is needed only when the $R_2$—C(O)-acyl group is not to be the same as R—C(O)-acyl group which is obtained earlier in the process.

Examples of anilines that can be used for reactio with the 1,2-cyclopentene oxide to form the 1-(anilino)2-hydroxy cyclopentane intermediates for making the N-(2-hydroxycycloalkyl)-N-anilides of this invention include:
aniline,
3,4-dichloroaniline,
3,5-dichloroaniline,
3-methyl-4-chloroaniline,
3-chloro-4-methylaniline,
3,4-dibromoaniline,
4-bromoaniline,
4-azidoaniline,
3-trifluoromethylaniline,
4-trifluoromethylaniline,
3-methoxyaniline,
3,5-dimethylaniline,
3-ethylaniline,
2-chloro-4-methylaniline,
3,4-dimethoxyaniline,
3-chloro-4-fluoroaniline,
3,4-dimethylaniline,
4-propylaniline, and the like.

Examples of orthoformates and carboxylic acid anhydrides which can be used to prepare the compounds of this invention include tri-$C_1$ to $C_3$-alkylorthoformate, such as trimethylorthoformate, acetic anhydride, propionic anhydride, n-butanoic acid anhydride, isobutanoic acid anhydride, cyclopropanecarboxylic acid anhydride, cyclobutanecarboxylic acid anhydride, cyclopentanecarboxylic acid anhydride, cyclohexanecarboxylic acid anhydride, acrylic anhydride, 2-butenoic acid anhydride, 2-pentenoic acid anhydride, and the like. The carboxylic acid halides useful for acylating the anilino nitrogen or the 2-hydroxy group of the cycloalkyl moiety include acetyl chloride or bromide, propionyl chloride or bromide, butyryl chloride or bromide, cyclobutanecarbonyl chloride or bromide, cyclohexanecarbonyl chloride or bromide, acryloyl chloride or bromide, methoxyacetyl chloride 2-butenoyl chloride or bromide, benzoyl chloride or bromide, phenylacetyl chloride and such phenylacetyl or benzoyl halides substituted on ring carbons thereof as defined above for Y' and Z', e.g., 4-trifluoromethylbenzoylchloride or bromide, 4-bromobenzoyl bromide, 3-trifluoromethylphenylacetylchloride, 3,4-dichlorophenylacetyl chloride, 3,4-dichlorobenzoyl chloride and the like.

Useful reagents for forming ether groups of the 2-hydroxycycloalkyl moieties of these compounds include methylbromide, methyl iodide, ethyl bromide or iodide, propyl bromide, 2-propenyl chloride or bromide, 2-butenyl bromide or iodide, 2-methyl-2-butenyl bromide, 2-pentenyl chloride or bromide, benzyl chloride or bromide, and benzyl substituted as defined for Y' and Z' above, such as, 3-trifluoromethylbenzyl chloride or bromide, 4-azidobenzyl chloride or bromide, 3,5-dimethylbenzyl iodide or bromide, 3,4-dichlorobenzyl iodide, 4-bromobenzyl bromide, 4-chlorobenzyl bromide or iodide and the like. Methods for ether preparation from alcohols and halides are known in the art and examples can be found in Buehler and Person, "Survey of Organic Syntheses", Wiley (1970), pp. 287–289. We have found that the most potent anti-depressant compounds are made from those compounds having an N-propionyl moiety so that in the formula I compounds, R is preferably ethyl.

Starting materials useful for purposes of this invention, if not commercially available, can be made by standard methods known in the chemical art.

If desired, the formula I compounds of this invention can be resolved into their respective d- and l-optical isomers by methods known in the art, for example in Organic Syntheses, Coll. Vol. 1, p. 418 (1946). The optical resolution of the compounds of the present invention can be done by at least two different routes:

By the first method for resolving the compounds of this invention, for example, one of the 2-hydroxycyclopentyl anilide compounds can be converted into its optically active diastereomeric salts by reaction with an optically inert esterifying agent (e.g., phthalic anhydride) followed by reaction with an optically active base, e.g., brucine, in a manner standard in the isomer resolution art. These diastereomeric salts can then be separated by conventional means such as differential crystallization. Diastereomeric salts have different crystallization properties, which are taken advantage of in this separation. On neutralization of each diastereomeric salt with aqueous acid followed by hydrolysis with base the corresponding optically active isomer of the free 2-hydroxycyclopentyl anilide can be obtained which can subsequently be converted to the corresponding optically active 2-ethers or 2-esters. By the second method, which in the case of some of these compounds is preferred, the N-(2-hydroxycyclopentyl)anilide derivative compound can be resolved into its respective d- and l-isomers by first resolving the unsymmetrically substituted 2-hydroxycyclopentylaniline into its respective d- and l-isomers by treatment with the resolving agent, such as optically active camphosulfonic acid, crystalization, separation and regeneration of each of the d- and l-isomers and then reacting the respective resolved d- or l-2-hydroxycyclopentylaniline starting material with the selected orthoformate or carboxylic acid anhydride or carboxylic acid halide to form the respective d- or l-isomers of the formula I compounds as the diacylated compounds which on subsequent basic hydrolysis give the respective optically active 2-hydroxycyclopentyl anilides which then can be converted as described in the Examples to other 2-ethers and 2-esters.

In the use of these compounds of formula I as anti-depressant drugs, the selected compound of formula I which is to be the anti-depressant active ingredient is mixed with suitable pharmaceutical diluents to obtain pharmaceutical compositions suited for oral, parenteral and rectal use in dosage unit form, e.g., tablets, powder packets, cachets, dragees, capsules, solutions, suspensions, sterile injectable forms, suppositories, bougies and the like. Suitable diluents or carriers such as carbohydrates (lactose), proteins, lipids, calcium phosphate, corn starch, stearic acid, methylcellulose and the like may be used as carriers or for coating purposes. Water and oils, e.g., coconut oil, sesame oil, safflower oil, cottonseed oil, peanut oil may be used for preparing solutions or suspensions of the active drug. Sweetening, coloring and flavoring agents may be added. The specifications for the dosage unit forms of these formula I compounds will vary somewhat from compound to compound and dependent upon the physical characteristics of the formula I compound, the particular patient's weight and age, and the particular effect sought to be achieved. The pharmaceutical dosage unit forms of these compounds are prepared in accordance with the preceding general description to provide from about 4 to about 400 mg. of the formula I compound per dosage unit form. The amount of the formula I compound prescribed in pharmaceutical dosage form is that amount sufficient to obtain in the patient a relief from the condition of depression effect at a non-toxic dosage level.

The following detailed procedures and examples further describe and illustrate how to make and use the starting amines and the compounds of this invention. All temperatures are in degrees Celsius unless otherwise indicated. For brevity, the term THF means tetrahydrofuran, DMF means N,N-dimethylformamide, NMR means nuclear magnetic resonance spectrum, IR means infrared spectrum, UV means ultraviolet spectrum, ether means diethyl ether, NaOH means sodium hydroxide, $MgSO_4$ means anhydrous magnesium sulfate, and MeOH means methanol.

EXAMPLE 1

Trans-N-(2-hydroxycyclopentyl)-3,4-dichloropropionanilide

Part A

A solution of 3,4-dichloroaniline (200 g., 1.23 mole), cyclopentene oxide (400 ml.) and concentrated HCl (2 ml.) is heated at reflux temperature for seven (7) days. The unreacted epoxide is evaporated at 60° C. and the residue is treated with excess ethereal HCl, and a syrup results. This is washed with 1000 ml. of ether. The residue is crystallized and recrystallized from methanol/ether (1/5.5, v/v) to give 170.0 g. (49% yield) of trans-3,4-dichloro-N-(2-hydroxycyclopentyl)aniline, hydrochloride salt.

Part B

A mixture of the amino alcohol, trans-N-(2-hydroxycyclopentyl)-3,4-dichloroaniline, released from its hydrochloride salt with 10% sodium hydroxide (61.5 g., 0.25 mole) and propionic anhydride (130 g., 1.0 mole) is heated on a stream bath for 72 hours. Water (250 ml.) is added and heating is continued for one hour. The mixture is cooled in an ice bath and then made basic by addition of 40% sodium hydroxide (140 ml.). The mixture is extracted with ethyl ether, the ether extract washed with brine, dried over magnesium sulfate and evaporated to a brown oily residue (95.0 g.) of the crude amide-ester, N-(2-acetoxycyclopentyl)-N-3,4-di-chloropropionanilide. This crude amine-ester oil is dissolved in a solution of potassium hydroxide (17.0 g., 85%, 0.25 mole) in 95% ethanol (250 ml.) and kept at room temperature for 3 hours. The solution is subjected to evaporation to remove solvent. The residue is treated with ether and extracted with water, 10% hydrochloric acid solution and brine. The organic layer is dried and evaporated to a brown solid. Recrystallization of the brown solid from an ether-petroleum ether mixture (b.p. 30°-60° C.) gives the titled compound, 49.5 g., 66% yield, m.p. 105° C., UV, IR, NMR and mass spectra are consistent with the assigned structure. Anal. calcd. for $C_{14}H_{17}Cl_2NO_2$:

Calcd.: C, 55.64; H, 5.67; N, 4.64; Cl, 23.46. Found: C, 55.84; H, 5.57; N, 4.81; Cl, 23.50.

EXAMPLE 2

Preparation of trans-3,4-dichloro-N-(2-methoxycyclopentyl)propionanilide

A mixture of 6.04 g. (0.02 mole) of trans-3,4-dichloro-N-(2-hydroxycyclopentyl)priopionanilide, (Example 1) 11.36 g. (0.08 mole) of methyl iodide, and 1.92 g. (50% dispersion, 0.04 mole) of sodium hydride in 75 ml. of DMF is stirred at room temperature overnight. The mixture is filtered through a filter aid (Celite ®) and the DMF solvent is removed from the filtrate by distillation at reduced pressure. The residue is dissolved in 250 ml. of ethyl ether and this solution is washed twice with water, followed by saturated aqueous sodium chloride solution, dried over anhydrous magnesium sulfate and concentrated to a yellow oil. Chromatography on silica gel with chloroform as eluent gives a center fraction (single component by thin layer chromatography) which is distilled to give 3.2 g. (50% yield) of the titled compound, b.p. 145°-150° C./0.01 mm. Hg.

Anal. calcd. for $C_{15}H_{18}NCl_2O_2$: Calcd.: C, 56.97; H, 6.06; N, 4.43; Cl, 22.42. Found: C, 57.02; H, 6.65; N, 4.37; Cl, 22.13.

EXAMPLE 3

Preparation of trans-N-(2-hydroxycyclopentyl)-propionanilide

Following the procedure of Example 1, but substituting a stoichiometrically equivalent amount of aniline for 3,4-dichloroaniline and adding a small quantity of water, there is obtained the titled compound, b.p. about 140° C./0.2 mm. Hg., 2.7 g., 36% yield.

Anal. calcd. for $C_{14}H_{19}NO_2$: Calcd.: C, 72.07; H, 8.21; N, 6.01. Found: C, 72.15; H, 8.37; N, 5.90.

EXAMPLE 4

Preparation of trans-3,4-dichloro-N-(2-acetoxycyclopentyl)propionanilide

A mixture of trans-3,4-dichloro-N-(2-hydroxycyclopentyl)propionanilide (3.02 g., 0.01 mole) (Example 1) and 10 ml. of acetic anhydride is heated on a steam bath for 3 hours. Additional heating for 1 hour is done after addition of 50 ml. of water. The reaction mixture is cooled, diluted with 50 ml. of water, and extracted with 200 ml. of ether. The ether extract is washed successively with water, saturated aqueous sodium bicarbonate solution and saturated aqueous sodium chloride, dried over anhydrous magnesium sulfate and is concentrated to a yellow oil. Distillation at reduced pressure gives 3.0 g. (37% yield) of the titled compound, b.p. 160°-165° C./0.3 mm. Hg. The Nuclear Magnetic Resonance (NMR) and IR spectra are consistent with the assigned structure.

Anal. calcd. for $C_{16}H_{19}NCl_2O_3$:

Calcd.: C, 55.82; H, 5.56; N, 4.07; Cl, 20.60. Found: C, 55.77; H, 5.51; N, 4.02; Cl, 21.07.

EXAMPLE 5

Preparation of trans-3,4-dichloro-N-(2-acetoxycyclopentyl)acetanilide

A mixture of 0.015 mole of trans-3,4-dichloro-N-(2-hydroxycyclopentyl)aniline (Example 1, Part A) free base and 25 ml. of acetic anhydride is heated on a steam bath overnight. After addition of 200 ml. of water, heating is continued for 30 minutes. The reaction mixture is cooled and extracted with 300 ml. of ethyl ether. The ether layer is washed sequentially with 100 ml. of 15% aqueous NaOH, 100 ml. of water, and 100 ml. of brine; the ether layer is then dried (MgSO$_4$) and evaporated to a yellow oil which is distilled to give 3.20 g. (66% yield) of the titled compound (b.p. 160° C./0.2 mm. Hg.).

Anal. calcd. for $C_{15}H_{17}NCl_2O_3$: Calcd.: C, 54.56; H, 5.19; N, 4.24; Cl, 21.47. Found: C, 54.39; H, 5.21; N, 4.27; Cl, 22.00.

EXAMPLE 6

Alternate preparation of trans-2-(3,4-dichloroanilino)cyclopentanol

A solution of 50.0 g. (0.31 mole) of 3,4-dichloroaniline in 100 ml. of cyclopentene oxide is refluxed for 7 days. The solution is evaporated and the residue triturated with 250 ml. of petroleum ether (b.p. 30°-60° C.) five times to remove unreacted 3,4-dichloroaniline. The residue is treated with excess ethereal hydrogen chloride and the resulting crude hydrochloride salt is recrystallized twice from a methanol/ethyl ether mixture to give trans-2-(3,4-dichloroanilino)cyclopentanol, 38.7 g. (44% yield), m.p. 167°-168° C. The ultraviolet, infrared and nuclear magnetic resonance spectra are consistent with the structure of this product.

Anal. calcd. for $C_{11}H_{13}Cl_2NO \cdot HCl$: Calcd.: C, 46.75; H, 4.99; N, 4.96; Cl, 37.64. Found: C, 46.79; H, 5.03; N, 4.97; Cl, 37.20.

EXAMPLE 7

Following the procedure of Example 1 but initially substituting a stoichiometrically equivalent quantity of 4-bromoaniline for 3,4-dichloroaniline there is obtained trans-4-bromo-N-(2-hydroxycyclopentyl)propionanilide.

EXAMPLE 8

Part A

Following the procedure of Example 1 but initially substituting a stoichiometrically equivalent quantity of 3-trifluoromethylaniline for 3,4-dichloroaniline, there is obtained 3-trifluoromethyl-N-(2-hydroxycyclopentyl)-propionanilide.

Part B

Following the procedure of Example 2 but substituting a stoichiometrically equivalent quantity of benzyl iodide (prepared separately, or in situ from benzyl bromide and crystalline potassium iodide) for methyl iodide, and the propionanilide from Part A (above) for the 3,4-dichloro-N-(2-hydroxycyclopentyl)propionanilide, there is obtained 3-trifluoromethyl-N-(2-benzyloxycyclopentyl)-propionanilide.

EXAMPLE 9

Following the procedure of Example 4 but initially substituting 4-bromobenzoylchloride for acetic anhydride there is obtained 3,4-dichloro-N-[2-(4-bromobenzoyloxy)-cyclopentyl]propionanilide.

EXAMPLE 10

Part A

Following the procedure of Example 1 but initially substituting a stoichiometrically equivalent quantity of 3-bromoaniline for 3,4-dichloroaniline there is obtained 3-bromo-N-(2-hydroxycyclopentyl)propionanilide.

Part B

Following the procedure of Example 4 but substituting the 3-bromo-N-(2-hydroxycyclopentyl)propionanilide for 3,4-dichloro-N-(2-hydroxycyclopentyl)propionanilide there is obtained 3-bromo-N-(2-acetoxycyclopentyl)propionanilide.

EXAMPLE 11

Part A

Following the procedure of Example 1, Part B, but substituting a stoichiometrically equivalent quantity of cyclopropanecarbonyl chloride for propionic anhydride, there is obtained 3,4-dichloro-N-(2-hydroxycyclopentyl)-cyclopropanecarboxanilide.

Part B

Following the procedure of Example 2 but using a stoichiometrically equivalent quantity of the starting material from Part A (above) in place of trans-3,4-dichloro-N-(2-hydroxycyclopentyl)propionanilide, there is obtained 3,4-dichloro-N-(2-methoxycyclopentyl)cyclopropanecarboxanilide.

For oral administration either solid or fluid unit dosage forms can be prepared. For preparing solid compositions such as tablets, the compound of formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Wafers are prepared in the same manner as tablets, differing only in shape and the inclusion of sucrose or other sweetener and flavor. In their simplest embodiment, capsules, like tablets, are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum, or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed from vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Rectal suppositories as used herein mean solid bodies for insertion into the rectum which melt or soften at body temperature releasing one or more pharmacologically or therapeutically active ingredients.

Pharmaceutically acceptable substances utilized in rectal suppositories are bases or vehicles and agents to raise the melting point.

Examples of bases or vehicles include, for example, cocoa butter (theobroma oil), glycerin-gelatin, carbowax (polyoxyethylene glycol) and appropriate mixtures of mono-, di-, and triglycerides of fatty acids. Combinations of the various bases may be used. Agents to raise the melting point of suppositories include, for example, spermaceti and wax. Rectal suppositories may be prepared either by the compressed method or by molding. The usual weight of a rectal suppository is 2.0 g.

Tablets and capsules for rectal administration are manufactured utilizing the same pharmaceutically acceptable substance and by the same methods as for formulations for oral administration.

Rectal suppositories, tablets or capsules are packaged either individually, in unit dose, or in quantity, multiple dose, for example, 2, 6 or 12.

The term unit dosage form, as used in the specification and claims, refers to physically discrete units suitable as unitary dosages for mammals including human subjects, each unit containing a predetermined quantity of active material calculated to produce the desired therapeutic effect in association with the required pharmaceutical diluent, carrier, or vehicle. The specifications for the novel unit dosage forms of this invention are dictated by and directly dependent on (a) the unique characteristics of the active material and the particular effect to be achieved, and (b) the limitations inherent in the art of compounding such an active material for use in humans, as disclosed in detail in this specification, these being features of the present invention. Examples of suitable unit dosage forms in accord with this invention are tablets, capsules, pills, suppositories, powder packets, granules, wafers, cachets, teaspoonsful, tablespoonsful, droppersful, ampuls, vials, segregated multiples of any of the foregoing, and other forms as herein described.

The dosage of the compound for treatment depends on route of administration, the age, weight and condition of the patient. A dosage schedule of from about 4 to about 400 mg., preferably 20 to 200 mg. per day, given in a single dose or in subdivided doses, embraces the effective range to alleviate depression for which the compositions are effective. The dosage to be administered is calculated on the basis of from about 0.08 to about 6 mg./kg. of weight of the subject, preferably from about 0.3 to about 3 mg./kg. The compound is compounded with a suitable pharmaceutical carrier in unit dosage form for convenient and effective administration. In the preferred embodiments of this invention, the dosage units can contain the compound in 10, 25, 30, 50 and 100 mg. amounts for systemic treatment. A sterile preparation of the active material contains 1% to 25% w/v for parenteral treatment. The dosage of compositions containing a compound of formula I and one or more other active ingredients is to be determined with reference to the actual dosage of each such ingredient.

In addition to the administration of a compound of formula I as the principal active ingredient of compositions for treatment of the conditions desired herein, the said compound can be combined with other compounds, such as analgesics, for example, aspirin, acetaminophen, PAC compound (phenacetin-aspirin-caffeine), anti-inflammatory agents, such as ibuprofen, and the like, anxiolytics, such as perphenazine, amitriptylene hydrochloride, chlordiazepoxide, alprazolam, doxepin hydrochloride and the like.

EXAMPLE 12

A lot of 10,000 tablets, each containing 25 mg. of trans-3,4-dichloro-N-(2-hydroxycyclopentyl)propionanilide as the active ingredient compound, is prepared from the following types and amounts of ingredients:

| | |
|---|---|
| Active ingredient compound | 250 g |
| Dicalcium phosphate | 1500 g |
| Methylcellulose, U.S.P. (15 cps.) | 60 g |
| Talc | 150 g |
| Corn Starch | 200 g |
| Magnesium stearate | 12 g |

The compound and dicalcium phosphate are mixed well, granulated with 7.5% solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in reducing depression in adults at a dose of 1 to 2 tablets per day, depending on the age and weight of the patient.

EXAMPLE 13

One thousand two-piece hard gelatin capsules, each containing 10 mg. of 3-bromo-N-[2-(acetoxy)cyclopentyl]propionanilide as the active ingredient compound, are prepared from the following types and amounts of ingredients:

| | |
|---|---|
| Active ingredient compound | 10 g |
| Lactose | 75 g |
| Talc | 25 g |
| Magnesium stearate | 1.5 g |

The ingredients are mixed well and filled into capsules of the proper size.

Capsules so prepared are useful for treating depression in adults at a dose of one to two capsules per day.

EXAMPLE 14

One thousand tablets for sublingual use are prepared from the following ingredients:

| | |
|---|---|
| 3-Trifluoromethyl-N-[2-(benzyloxy)cyclopentyl]propionanilide | 100 g |
| Active ingredient compound, micronized | 5 g |
| Polyethylene glycol 4000, powdered | 150 g |
| Polyethylene glycol 6000, powdered | 75 g |

The ingredients are mixed well and compressed into sublingual-type tablets.

These tablets (each containing 100 mg. of active ingredient) placed under the tongue are useful to reduce depression with a rapid induction at a dose of one tablet per 6 hours.

EXAMPLE 15

Soft gelatin capsules for oral use, each containing 30 mg. of 3,4-dichloro-N-(2-methoxycyclopentyl)propionanilide, are prepared by first dispersing the micronized compound in corn oil to render the material capsulatable and then encapsulating in the usual manner. These capsules are useful in treatment of depression at a dose of one to two capsules a day.

EXAMPLE 16

One thousand tablets, each containing 50 mg. of 3,4-dichloro-N-[2-(4-bromobenzoyloxy)cyclopentyl]propionanilide are made from the following types and amounts of ingredients:

| | |
|---|---|
| 3,4-dichloro-[2-(4-bromobenzoyloxy)cyclopentyl]propionanilide | 50 g |
| Lactose | 355 g |
| Microcrystalline cellulose NF | 120 g |
| Starch | 16 g |
| Magnesium stearate powder | 4 g |

The ingredients are screened and blended together and pressed into tablets.

The tablets are useful to overcome depression.

EXAMPLE 17

A sterile preparation suitable for intramuscular injection and containing 50 mg. of 4-bromo-N-[2-hydrocyclopentyl]propionanilide, in each millititer is prepared from the following ingredients.

| | |
|---|---|
| 4-Bromo-N-[2-hydroxycyclopentyl]propionanilide | 50 g |
| Benzyl benzoate | 200 ml. |
| Methylparaben | 1.5 g |
| Propylparaben | 0.5 g. |
| Cottonseed oil q.s. | 1,000 ml. |

One milliliter of this sterile preparation is injected to reduce depression in adults.

EXAMPLE 18

Following the procedure of the preceding Examples 12 through 17, inclusive, unit dosage forms are similarly prepared substituting equivalent amounts of other formula I compounds, for example, the trans isomers of:
3-Chloro-4-methyl-N-(2-hydroxycyclopentyl)propionanilide, 3,4-Dichloro-N-(2-ethoxycyclopentyl)propionanilide,
3,4-Dimethoxy-N-(2-propoxycyclopentyl)propionanilide,
3-Chloro-4-fluoro-N-(2-methoxycyclopentyl)propionanilide,
3,4-Dibromo-N-(2-benzyloxycyclopentyl)propionanilide,
3,4-Dimethyl-N-(2-benzoyloxycyclopentyl)propionanilide,
3,4-Dichloro-N-[2-(4-bromobenzyloxy)cyclopentyl]cyclopropanecarboxanilide,
4-Bromo-N-(2-hydroxycyclopentyl)acrylanilide,
3,4-Dichloro-N-[2-(3,4-dichlorobenzoyloxy)cyclopentyl]propionanilide,
3-Methoxy-N-(2-hydroxycyclopentyl)propionanilide,
3-Chloro-4-methyl-N-[2-(4-chlorobenzyloxy)cyclopentyl]propionanilide,
3,4-Dichloro-N-[2-(4-bromobenzyloxy)cyclopentyl]acetanilide,
3,4-Dichloro-N-[2-(3-chloro-4-methylbenzyloxy)cyclopentyl]cyclohexanecarboxanilide,
4-Azido-N-(2-hydroxycyclopentyl)propionanilide,
4-Azido-N-[2-(3,4-dichlorophenoxy)cyclopentyl]propionanilide,
4-Azido-N-[2-(3-chloro-4-methylbenzyloxy)cyclopentyl]-n-butanoylanilide,
4-Azido-N-[2-(benzoyloxy)cyclopentyl]acetanilide,
4-Azido-N-[2-(3,4-dichlorobenzoyloxy)cyclopentyl]propionanilide,
4-Azido-N-[2-(propionyloxy)cyclopentyl]cyclopentanecarboxanilide,
4-Azido-N-[2-(allyoxyl)cyclopentyl]methoxyacetanilide, and the like, for the respective active ingredients in those examples.

What is claimed is:

1. A compound of the formula

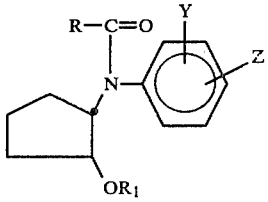

wherein the heavy dot (•) at the 1-position carbon atom of the cyclopentyl ring denotes the trans-configuration relative to the oxygen group (—OR$_1$) in the 2-position of the cyclopentyl ring;
R is C$_1$ to C$_3$-alkyloxy or C$_1$ to C$_3$-alkyloxymethyl;
R$_1$ is hydrogen, C$_1$ to C$_3$-alkyl, C$_3$ to C$_5$-(allyllic)alkenyl, the benzyl group

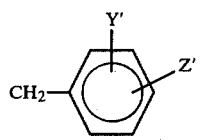

wherein Y' and Z' are as defined above, or the group

wherein R$_2$ is hydrogen, C$_1$ to C$_3$-alkyl, the benzyl group as above, or a phenyl group

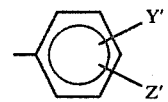

wherein Y' and Z' are as defined hereinbelow; and each of Y and Z or Y' and Z' is selected from the group consisting of hydrogen, a halogen having an atomic number of from 9 to 35, trifluoromethyl, C$_1$ to C$_3$-alkyl, and C$_1$ to C$_3$-alkyloxy, and Y, Z, or Y' and Z' are not necessarily the same at the same time.

2. A process for treating depression which comprises administering to a depressed human a compound of the formula

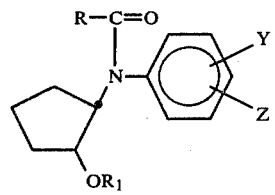

wherein the heavy dot (•) at the 1-position of the cyclopentyl ring denotes the trans-configuration relative to the oxygen group (—OR$_1$) in the 2-position of the cyclopentyl ring;
R is C$_1$ to C$_3$-alkyloxy or C$_1$ to C$_3$-alkyloxymethyl;
R$_1$ is hydrogen, C$_1$ to C$_3$-alkyl, C$_3$ to C$_5$-(allylic)alkenyl, the benzyl group

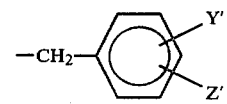

wherein Y' and Z' are as defined below, or the group,

where R$_2$ is hydrogen, C$_1$ to C$_3$-alkyl, the benzyl group as defined above or the phenyl group

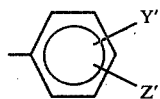

wherein Y' and Z' are as defined below, each of Y, Z, Y' and Z' is selected from the group consisting of hydrogen, halogen having an atomic number of from 9 to 35, trifluoromethyl, C$_1$ to C$_3$-alkyl, and C$_1$ to C$_3$-alkyloxy, and Y, Z, Y' and Z' are not necessarily the same at the same time, in a non-toxic amount effective to alleviate the conditions of depression, in association with a pharmaceutical carrier.

3. A pharmaceutical preparation in dosage unit form adapted for administration to obtain an anti-depression effect comprising per dosage unit, an anti-depressant effective, non-toxic amount of a compound of the formula

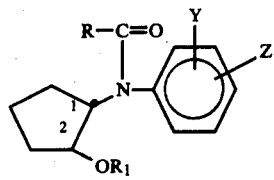

wherein the heavy dot (•) at the 1-position carbon atom of the cyclopentyl ring denotes the trans-configuration relative to the oxygen group (—OR$_1$) in the 2-position of the cyclopentyl ring;

R is C$_1$ to C$_3$-alkyloxy or C$_1$ to C$_3$-alkyloxymethyl;

R$_1$ is hydrogen, C$_1$ to C$_3$-alkyl, C$_3$ to C$_4$-(allylic)alkenyl, the benzyl group

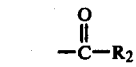

wherein Y' and Z' are as defined below, or the group $$-\overset{O}{\underset{\|}{C}}-R_2$$

where R$_2$ is hydrogen, C$_1$ to C$_3$-alkyl, the benzyl group as above, or a phenyl group

wherein Y' and Z' are as defined hereinbelow:

and each of Y and Z or Y' and Z' is selected from the group consisting of hydrogen, halogen having an atomic number of from 9 to 35, trifluoromethyl, C$_1$ to C$_3$-alkyl and C$_1$ to C$_3$-alkyloxy, and Y, Z, Y' and Z' are not necessarily the same at the same time.

4. A composition according to claim 3 wherein compound of formula I is present in an amount ranging from about 4 to about 400 mg. per dosage unit.

* * * * *